United States Patent [19]
Bayne et al.

[11] Patent Number: 5,532,343
[45] Date of Patent: Jul. 2, 1996

[54] PURIFICATION AND CHARACTERIZATION OF A GLIOMA-DERIVED GROWTH FACTOR HAVING VASCULAR ENDOTHELIAL CELL GROWTH PROMOTING ACTIVITY

[75] Inventors: Marvin L. Bayne, Westfield; Kenneth A. Thomas, Jr., Chatham Borough, both of N.J.; Gregory L. Conn, Bedfords Hills, N.Y.

[73] Assignee: Merck & Co., Inc., Rahway, N.J.

[21] Appl. No.: 204,850

[22] Filed: Mar. 2, 1994

Related U.S. Application Data

[62] Division of Ser. No. 889,547, May 27, 1992, Pat. No. 5,338,840, which is a continuation of Ser. No. 500,421, Mar. 30, 1990, abandoned, which is a continuation-in-part of Ser. No. 356,477, May 24, 1989, abandoned.

[51] Int. Cl.$^6$ .................. C07K 14/475; C07K 14/515
[52] U.S. Cl. ............................ 530/399; 530/350
[58] Field of Search ............................. 530/399, 350; 574/2; 435/69.1

[56] References Cited

U.S. PATENT DOCUMENTS

| | | |
|---|---|---|
| 4,456,550 | 6/1984 | Dvorak et al. . |
| 4,665,037 | 5/1987 | Stolowitz . |
| 5,194,596 | 3/1993 | Tischer et al. . |
| 5,219,739 | 6/1993 | Tischer et al. . |
| 5,338,840 | 8/1994 | Bayne et al. . |

FOREIGN PATENT DOCUMENTS

| 0370989 | 5/1990 | European Pat. Off. . |
|---|---|---|
| WO90/13649 | 11/1990 | WIPO . |
| WO91/02058 | 3/1991 | WIPO . |

OTHER PUBLICATIONS

Conn, G. L., Endothelial Cell Growth Factors Yeshiva University, New York, 1987 (Cumulative).
Stryer, Biochemistry, W. H. Freeman & Co., San Francisco, 1981 p. 629 (Cumulative).
Conn, G. H. et al., 1990, Amino Acid and CDNA Sequences of a Vascular Endothelial Cell Mitogen that is Homologous to Platelet-Derived Growth Factor, P.N.A.S. U.S.A., Vol. 87, p. 2628 (Culmulative).
Hammacher et al., 1988, A Human Glioma Cell Line Secretes Three Structurally and Functionally Different Forms of Platelet Derived Growth Factor, Eur. J. Biocjem., vol. 176, p. 179 (Cumulative).
Liberman et al., 1987, An Angiogenic Growth Factor is Expressed in Human Glioma Cells, EMBO J., vol. 6, p. 1627 (Cumulative).
Nister et al., 1988, A Glioma Derived PDGF a Chain Homodimer Has Different Functional Activities From a PDGF AB Heterodimer Purified From Human Platelets, Cells, vol. 52, p. 791 (Cumulative).

*Primary Examiner*—Stephen G. Walsh
*Assistant Examiner*—Karin Cochrane Carlson
*Attorney, Agent, or Firm*—John W. Wallen, III; Jack L. Tribble

[57] ABSTRACT

Glioma-derived growth factor is purified from the culture media used to maintain mammalian glioma cells. The protein stimulates mitogenesis of mammalian vascular endothelial cells and is useful for the promotion of vascular development and repair. This unique growth factor is also useful in the promotion of tissue repair.

2 Claims, 5 Drawing Sheets

FIG.1

```
─────────── p5-15 ───────────
A ACC ATG AAC TTT CTG CTC TCT TGG GTG CAC CTG GCT TTA CTG CTG TAC CTC CAC CAT
  1                                                                        20
  MET-ASN-PHE-LEU-LEU-SER-TRP-VAL-HIS-LEU-ALA-LEU-LEU-LEU-TYR-LEU-HIS-HIS-

─────────── p5-15 ───────────
GCC AAG TGG TCC CAG GCT GCA CCC ACG ACA GAA GGG GAG CAG AAA GCC CAT GAA GTG GTG
 21                                  30                                        40
 ALA-LYS-TRP-SER-GLN-ALA-[ALA-PRO-THR-THR-GLU-GLY-GLU-GLN-LYS-ALA-HIS-GLU-VAL-VAL-
                          ↑↑↑ ↑↑↑ ↑↑↑ ↑↑↑ ↑↑↑ ↑↑↑ ↑↑↑ ↑↑↑ ↑↑↑ ↑↑↑ ↑↑↑ ↑↑↑ ↑↑↑
                          ↕↕↕                                          ↕
                          V11A                                        L12
                          └──────────────── T27 ────────────────┘
                          └──────────────────── CB26 ──────────────────────

─────────── p5-15 ───────────                                    ↓ p4238
AAG TTC ATG GAC GTC TAC CAG GCT AGC TAT TGC CGC CCG ATT GAG ACC CTG GTG GAC ATC
 41                                  50                                        60
 LYS-PHE-MET-ASP-VAL-TYR-GLN-ALA-SER-TYR-CYS-ARG-PRO-ILE-GLU-THR-LEU-VAL-ASP-ILE-
 ↑↑↑ ↑↑↑ ↑↑↑ ↑↑↑ ↑↑↑ ↑↑↑ ↑↑↑ ↑↑↑ ↑↑↑ ↑↑↑ ↑↑↑ ↑↑↑ ↑↑↑ ↑↑↑ ↑↑↑ ↑↑↑ ↑↑↑ ↑↑↑ ↑↑↑ ↑↑↑
 ↕↕↕                       ↕                              ↑↑↑
 T41                      T65
 └──── L42 ────┘
 └──────────── V40 ────────────┘
 ──── CB26 ────→
```

FIG. 1a

```
                                                              p4238
TTC CAG GAG TAC CCC GAT GAG ATA GAG TAT ATC TTC AAG CCG TCC TGT GTG CCC CTA ATG
 61                                                                            80
PHE-GLN-GLU-TYR-PRO-ASP-GLU-ILE-GLU-TYR-ILE-PHE-LYS-PRO-SER-CYS-VAL-PRO-LEU-MET-
                                        T65
                                              L42
                                                    V30 p4238
CGG TGT GCG GGC TGC TGC AAT GAT GAA GCC CTG GAG TGC GTG CCC ACG TCG GAG AGC AAC
 81                                                                           100
AAG-CYS-ALA-GLY-CYS-CYS-ASN-ASP-GLU-ALA-LEU-GLU-CYS-VAL-PRO-THR-SER-GLU-SER-ASN
                                        L42
                                              V30 p4238
GTC ACT ATG CAG ATC ATG CGG ATC AAA CCT CAC CAA AGC CAG CAC ATA GGA GAG ATG AGC
101                                                                           120
VAL-THR-MET-GLN-ILE-MET-ARG-ILE-LYS-PRO-HIS-GLN-SER-GLN-HIS-ILE-GLY-GLU-MET-SER-
                                        L42
                                    V18R
                                              CB18-19
```

PURIFICATION AND CHARACTERIZATION OF A GLIOMA-DERIVED GROWTH FACTOR HAVING VASCULAR ENDOTHELIAL CELL GROWTH PROMOTING ACTIVITY

This is a division of application Ser. No. 07/899,547 filed May 27, 1992, now U.S. Pat. No. 5,338,840 which is a continuation of Ser. No. 07/500,421 filed Mar. 30, 1990, now abandoned, which is a continuation-in-part of Ser. No. 07/356,477 filed May 24, 1989, now abandoned.

BACKGROUND OF THE INVENTION

Endothelial cell mitogens are useful in promoting vascular tissue repair in vivo, such as blood vessel growth (angiogenesis), and vessel repair (through the replacement of damaged endothelial cells) and in stimulating endothelial cell growth on appropriate substrates for the production of blood vessels for implantation. Glioma-derived growth factor (GDGF) treatment permits the covering of synthetic polymeric vessels with non-thrombogenic vascular endothelial cells from the host animal, including man, whereby many or all of the clotting problems associated with synthetic vessel grafts are obviated. Endothelial cell stimulation with GDGF is useful for the production of vessels in vitro by growth of host vascular endothelial cells on tubular supports, for implantation back into the same host animal, including man, whereby immunological rejection of the implant will be obviated and the frequent limited supply of good vessels within the patient for transplant will be obviated. Tubular supports are coated in vitro with GDGF prior to either implantation into a host animal or coated and seeded with endothelial cells and implanted. Following implantation endothelial cells migrate into and/or grow on the artificial surface producing in vivo artificial vessels. As noted above GDGF can also be used for the stimulation or facilitation of blood vessel growth and repair in vivo, whereby the flow of blood to tissues deprived of adequate oxygen and/or other blood borne components is increased. Since GDGF can enhance vascular development and growth by the specific stimulation of vascular endothelial cells the protein can be useful in stimulating tissue repair.

OBJECTS OF THE INVENTION

It is, accordingly, an object of the present invention to provide a novel glioma-derived growth factor (GDGF). Another object is to provide a procedure for the purification of the substantially pure GDGF. A further object is to provide GDGF to stimulate endothelial cells for induction of blood vessel growth, vascular repair and the production of artificial blood vessels.

SUMMARY OF THE INVENTION

Glioma-derived growth factor is purified from the culture media used to maintain mammalian glioma cells. The protein stimulates mitogenesis of mammalian endothelial cells and is useful for the promotion of vascular development and repair. This unique growth factor is also useful in the promotion of tissue repair.

DETAILED DESCRIPTION

The present invention relates to a unique glioma derived growth factor (GDGF) which exhibits mitogenic stimulation of endothelial cells. Glioma is defined herein as any neoplasm derived from one of the various types of cells that form the interstitial tissue of the central nervous system including brain, spinal cord, posterior pituitary gland and retina. Consequently, the scope of the present invention is intended to include the unique growth factor isolated and purified from any mammalian glioma tissue or cells including cell lines. Cell lines include, but are not limited to, glioma-derived cell lines such as C6, hs 683 and GS-9L; glioblastomas such as A-172 and T98G; neuroblastomas such as IMR-32 and SK-N-MC; neurogliomas such as H4; tetromas such as XB-2; astrocytomas such as U-87 MG and U-373 MG; embryonal carcinomas and non-transformed glial or astrocyte cell lines, with GS-9L being preferred. Anterior pituitary tumor cell lines such as GH3 and Hs 199 may also be used. Although the GDGF of this invention is described as being isolated from rat cells, the same or substantially similar growth factor may be isolated from other mammalian cells, including human cells.

Glioma-derived growth factor exists in various microheterogeneous forms which are isolated from one or more of the various cells described above. Microheterogeneous forms as used herein refer to a single gene product, that is a peptide produced from a single gens unit of DNA, which is structurally modified at the mRNA level or following translation. Peptide and protein are used interchangeably herein. The microheterogeneous forms will all have equivalent mitogenic activities. Biological activity and biologically active are used interchangeably and are herein defined as the ability of GDGF to stimulate DNA synthesis in target cells including vascular endothelial cells as described below which results in cell proliferation. The modifications may take place either in vivo or during the isolation and purification process. In vivo modification results from, but is not limited to, proteolysis, glycosylation, phosphorylation, acetylation or deamidation at the N-terminus. Proteolysis may include exoproteolysis wherein one or more terminal amino acids are sequentially, enzymatically cleaved to produce microheterogeneous forms which have fewer amino acids than the original gene product. Proteolysis may also include endoproteolytic modification that results from the action of endoproteases which cleave the peptide at specific locations within the amino acid sequence. Similar modifications can occur during the purification process which also results in production of microheterogeneous forms. The most common modification occurring during purification is proteolysis which is generally held to a minimum by the use of protease inhibitors. Under most conditions one or more microheterogeneous forms are present following purification of native GDGF. Native GDGF refers to GDGF isolated and purified from cells that produce GDGF.

Glioma cells such as the rat cell line GS-9L are grown to confluence in tissue culture flasks, about 175 cm$^2$, in Dulbecco's Modified Eagle's Medium (DMEM) supplemented with about 10% newborn calf serum (NCS). When the cells reach confluence the culture medium is removed, the cell layers washed with Ca, Mg-free phosphate buffered saline (PBS) and removed from the flasks by treatment with a solution of trypsin, about 0.1%, and EDTA, about 0.04%. The cells, about 1×10$^8$, are pelleted by centrifugation, resuspended in about 1500 ml of DMEM containing about 5% NCS and plated into a ten level cell factory (NUNC), 6,000 cm² surface area. The cells are incubated for about 48 to about 96 hours, with 72 hours preferred, at about 37° C. in an atmosphere of about 5% $CO_2$. Following incubation the medium is removed and the cell factories are washed 3 times with PBS. Fresh culture media, about 1500 ml of about a 1:2 mixture of Ham's-F12/DMEM containing about 25 mMHepes, about 5 µg/ml insulin, about 10 µg/ml transfertin and with or without about 1.0 mg/ml bovine serum albumin. This media is replaced with fresh media after about 24 hr and collected ever 48 hr thereafter. The collected conditioned media is filtered through Whatmen #1 paper to remove cells debris and stored at −20° C.

The GS-9L conditioned media is thawed and brought to pH 6.0 with 1 M HCl. The initial purification step consists of cation exchange chromatography using a variety of cation exchangers on a variety of matrices such as CM Sephadex, Pharmacia Mono S, Zetachrom SP and Polyaspartic Acid WCX (Nest Group) with CM Sephadex C-50 (Pharmacia) being preferred. The GDGF-containing culture media is mixed with CM Sephadex C-50 at about 1 gm per about 20 L of the conditioned media and stirred at low speed for about 24 hr at 4° C. The resin is allowed to settle and the excess liquid is removed. The resin slurry is packed into a column and the remaining culture media is removed. Unbound protein is washed from the column with 0.05M sodium phosphate pH 6.0 containing 0.15M NaCl. The GDGF is eluted with about 0.05M sodium phosphate pH 6.0 containing about 0.6M NaCl.

The active fractions collected from the CM Sephadex C-50 column are further fractionated by lectin affinity chromatography for additional purification of GDGF. The lectins which may bind GDGF include, but are not limited to, lectins which specifically bind mannose residues such as concanavalin A and lens culinaris agglutinin, lectins which bind N-acetylglucosamine such as wheat germ agglutinin, lectins that bind galactose or galactosamine and lectins which bind sialic acids, with concanavalin A (Con A) being preferred. A 1.5 cm diameter column containing about 5 ml packed volume of Con A agarose (Vector Laboratories) is washed and equilibrated with about 0.05M sodium acetate about pH 6.0 containing about 1 mM $CaCl_2$, about 1 mM $MnCl_2$ and about 0.6M NaCl. The unbound protein is washed from the column with equilibration buffer. The GDGF is eluted with equilibration buffer containing about 0.5M α-methyl mannoside.

The GDGF active fractions collected from the Con-A column are diluted about 1:2 with about 0.05M sodium phosphate about pH 6.0. The sample is applied to a Polyaspartic Acid WCX cation exchange high performance liquid chromatography (HPLC) column equilibrated with the same phosphate buffer at a rate of about 0.5 ml/min. The column is eluted with a linear gradient of about 0 to 100% of about 0.75M NaCl in the same buffer. The flow rate is maintained at about 0.75 ml/min and the fractions are collected every 60 seconds. Glioma-derived growth factor is present in fractions eluting between approximately 25 and 30 min.

The fractions containing GDGF activity eluted from the Polyaspartic Acid WCX column are loaded onto a 4.5×50 mm Vydac $C_4$ reverse phase HPLC column previously equilibrated in solvent A 0.1% trifluoroacetic acid (TFA). The column is eluted with a linear gradient over 60 min of 0 to 100% B, where B=33% A+67% acetonitrile (v/v). The flow rate is maintained at 0.75 ml/min and fractions are collected every minute. The homogeneous GDGF elutes from the $C_4$ column under these conditions at between 29 and 32 minutes. The growth factor is eluted into about 150 µl of about 1M Hepes buffer about pH 7.55 per 750 µl of column eluate.

Purity of the protein is determined by sodium dodecylsulfate (SDS) polyacrylamide gel electrophoresis (PAGE) in 12.5% crosslinked gels using the technique of Laemmli, Nature 227:680–684 (1970). The silver stained gels show GDGF to consist of one or more bands under non-reducing conditions with approximate molecular masses in the range of about 48,000 to about 44,000 daltons. When a sample containing the microheterogeneous forms of GDGF is separated under reducing conditions GDGF migrates as a single band with a molecular mass of about 21,000 daltons.

Glioma-derived growth factor can also be extracted from non-reducing sodium dodecyl sulfate polyacrylamide gels after electrophoresis. Electrophoresis is carried out under conditions known in the art. The GDGF is eluted from the gel with buffer and the protein concentrated in a Centricon-10 centrifugal microconcentrator or an equivalent.

Biological activity is determined by mitogenic assay using mammalian vascular endothelial cells. Human umbilical vein endothelial (HUVE) cells are plated on gelatin coated dishes at a density of about 2000 cells per cm² in about 500 µl of Medium 199 (M199) containing about 20% heat-inactivated fetal calf serum (FCS) and about 15 mMHepes buffer, about pH 7.55. Samples of GDGF are serially diluted in M199 plus FCS and added to the wells at the time of plating. The cells are incubated at 37° C. under 5% $CO_2$ for 72 hr. After incubation the medium is removed, the cells are washed with about 250 µl of PBS, about pH 7.4 and the cells are detached with about 200 µl trypsin, about 0.1%/EDTA, about 0.04%. The cell are then counted in a hemocytometer. The concentration of GDGF which elicits a half-maximal mitogenic response is approximately 1 ng/ml.

Bovine aortic endothelial cells (BAEC) are used to evaluate thymidine incorporation following GDGF treatment. BAEC are plated at a density of about 2000 cells/well in about 500 µl of DMEM containing 10% NCS and incubated at 37° C. for 12 hr. The medium is removed and replaced with DMEM plus 1% FCS and the cells incubated for 48 hr. Samples of GDGF are serially diluted in DMEM containing 1% FCS and added at the end of the 48 hr period. After a further 12 hr of incubation 1.6 of [methyl-³H]-thymidine (20 Ci/mmol) and 2.45 µg of unlabeled thymidine per ml of medium is added to the wells in 20 µl of DMEM. The cells are incubated for 36 hr, washed with PBS and lysed with 250 µL of a solution of 2 g sodium carbonate and 0.4 g NaOH per 100 ml. The amount of incorporation of radiolabel into cellular DNA is determined by scintillation counting.

Samples of the native dimeric GDGF, 48 kilodalton (kDa), 46 kDa and 44 kDa, and a sample of the reduced and carboxymethylated monomer (21 kDa) are hydrolyzed for about 24 hr in constant boiling 6N HCl and their amino acid compositions determined using the Waters Pico Tag system. The amino acid composition is shown in Table 2.

A sample of purified GDGF is reduced in about 0.1M Tris pH about 9.5 with about 0.1% EDTA, about 6M guanidinium chloride and about 20 mM dithiothreitol for about 2 hr at about 50° C. The reduced protein is carboxymethylated by the addition of about 9.2 µM of unlabelled and 2.8 µM of ¹⁴C-iodoacetic acid in about 0.7M Tris about pH 7.8 containing about 0.1% EDTA and about 6M guanidinium chloride. The protein is carboxymethylated for about 1 hr at room temperature. The protein was isolated by reverse phase HPLC as described above. A sample of the reduced and carboxymethylated monomer was treated with either the protease trypsin which cleaves polypeptides on the C-terminal side of lysine and arginine residues or Lys C which cleaves polypeptides on the C-terminal side of lysine by procedures well known in the art. The peptides are isolated by reversed phase -HPLC(RP-HPLC). The amino acid sequences of the isolated peptides are determined using the Edman degradation in the ABI gas phase sequenator in conjunction with the ABI 120 A on line phenylthiohydantoin analyzer following manufacturer's instructions. The amino acid sequences are shown in Table 3.

Reduced and carboxymethylated GDGF is dried and solubilized in about 0.7M Tris, about pH 7.8, about 6M guanidinium chloride containing about 0.1% EDTA. V8 protease is added in an ammonium bicarbonate buffer, about pH 8.0 and the mixture incubated for about 48 hr at about 37° C. The protease cleaves predominantly on the carboxyl termina side of glutamic acid residues. The resulting polypeptides were resolved by $C_{18}$ RF-HPLC as above.

Following reduction and carboxymethylation of GDGF the protein solution is adjusted to a pH of about 6.8 with 6 N HCl and dithiotreitol is added to a final concentration of 2M for reduction of any methionine sulfoxide to methionine residues. After about 20 hr of reduction at about 39° C. the protein is repurified by $C_4$HPLC. The product is dried and cleaved on the carboxyl terminial side of methionine residues by 200µl of 40 mM cyanogen bromide in about 70% (v/v) formic acid under an argon atmosphere at about 20° C. for about 24 hr in the dark. The cleavage products are resolved by $C_{18}$ RP-HPLC. The amino acid sequence is shown in FIG. 1.

Figure 1:
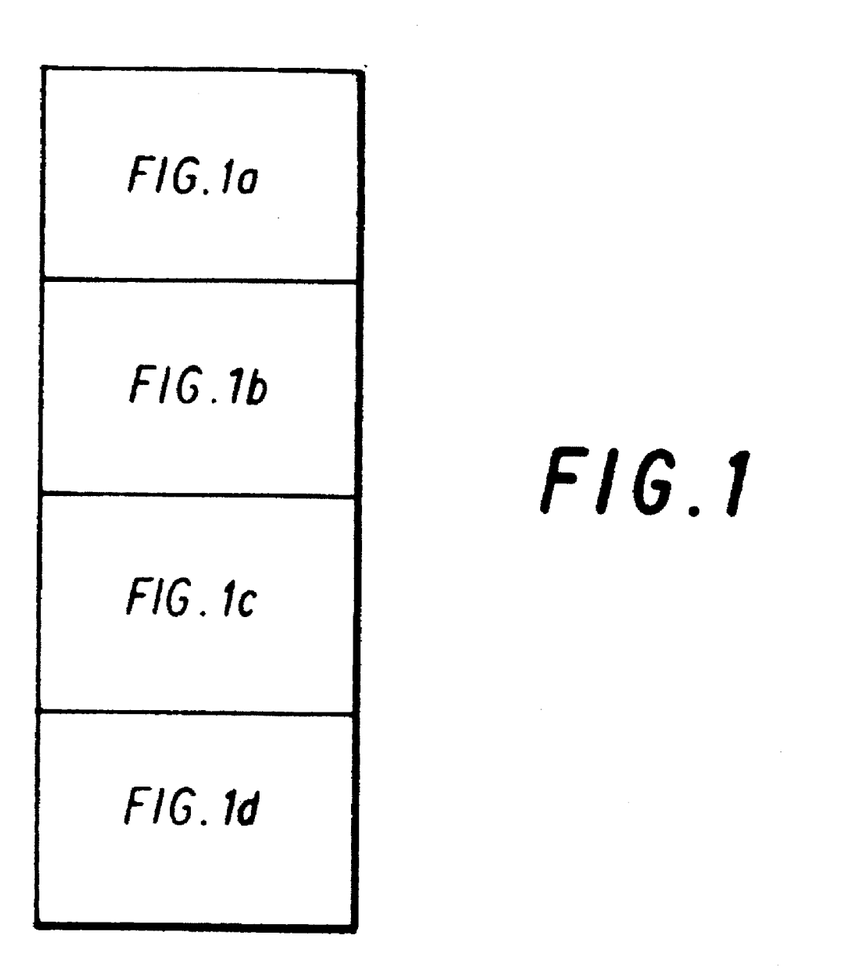
FIG. 1 is a depiction of the relationship of FIGS. 1a–1d.
Figure 1A:
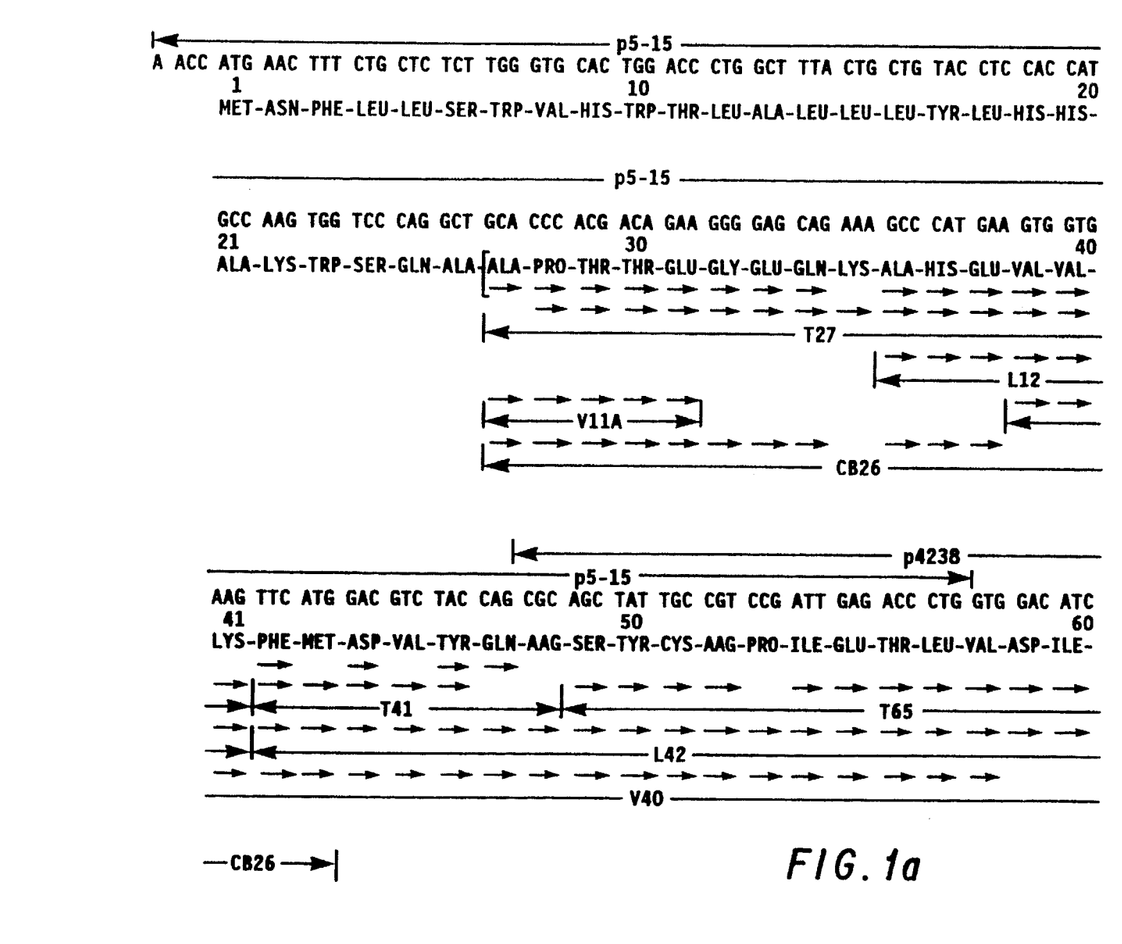
FIG. 1a–1d shows and the full length 190 amino acid residue protein translation product and its cDNA coding sequence.
Figure 1B:
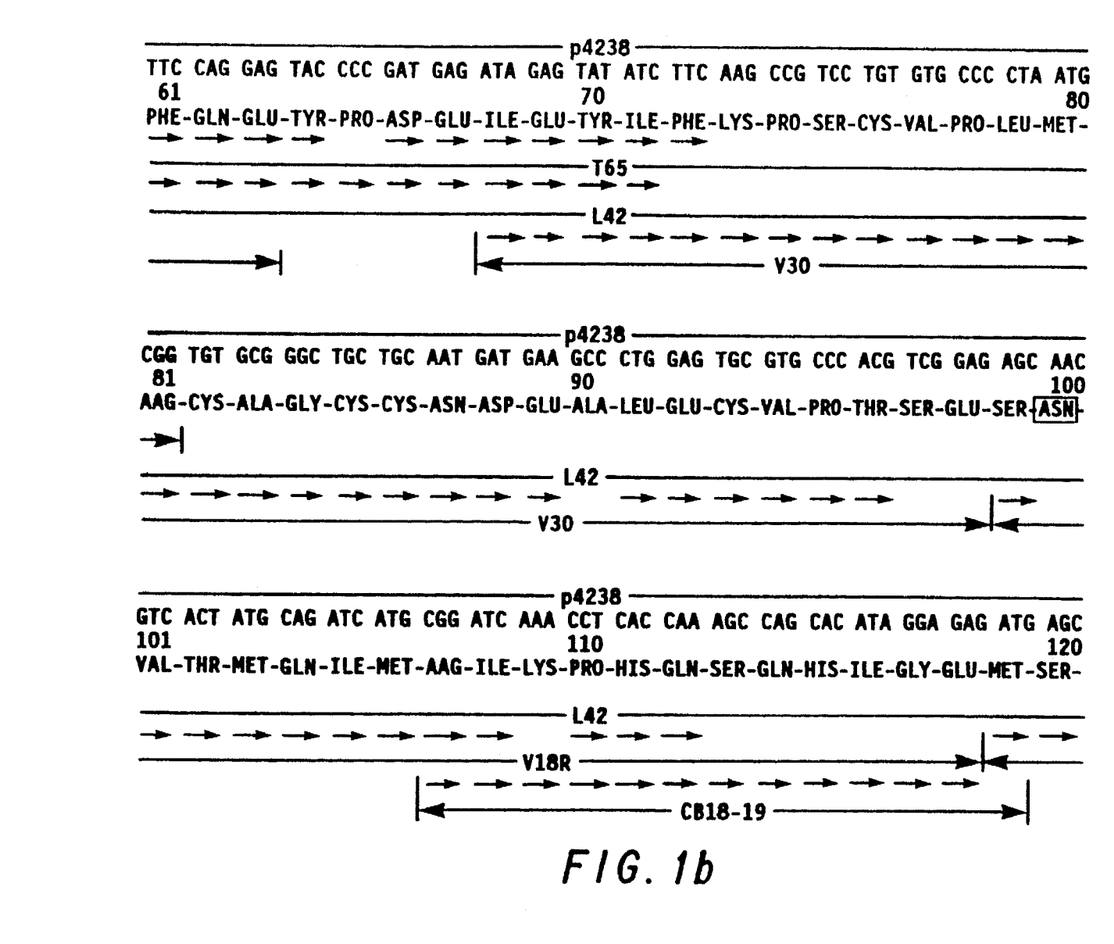
Figure 1C:
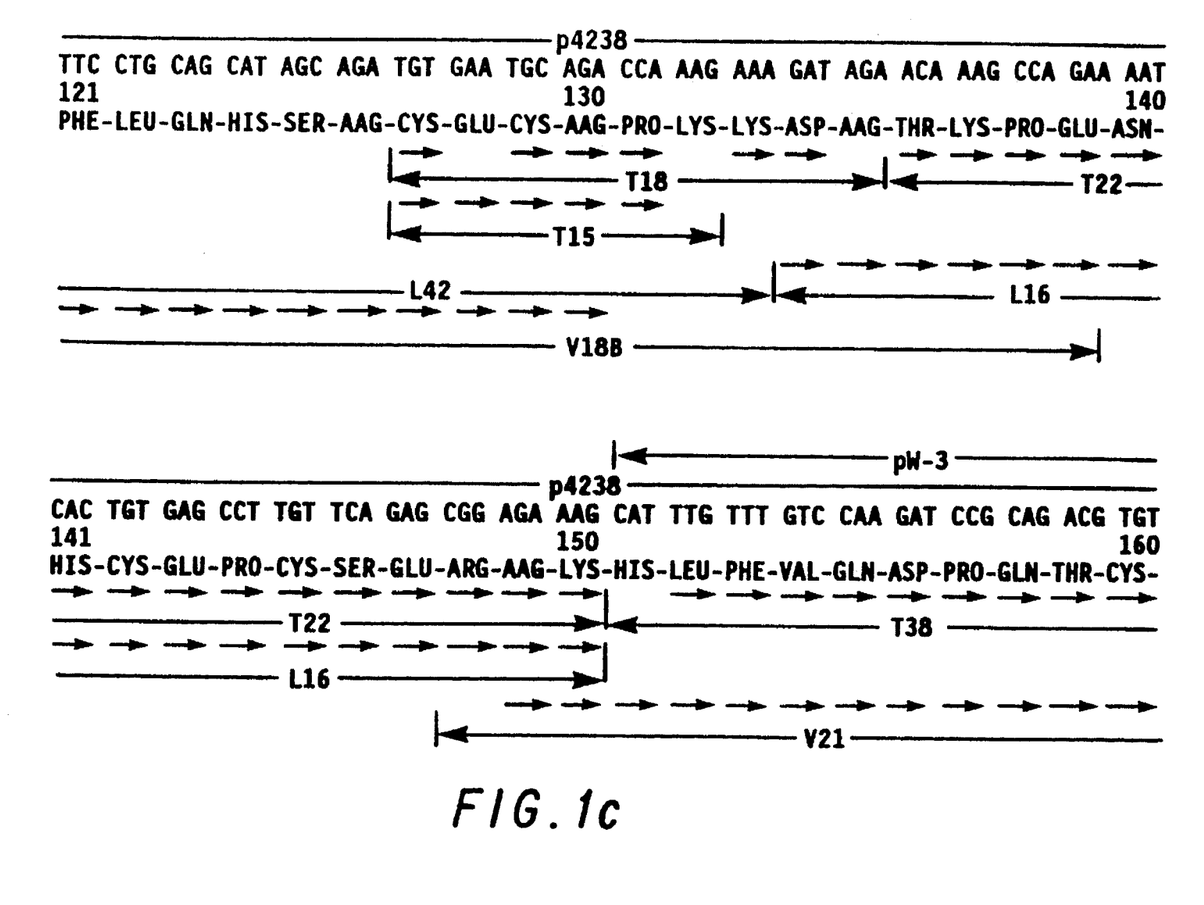
Figure 1D:
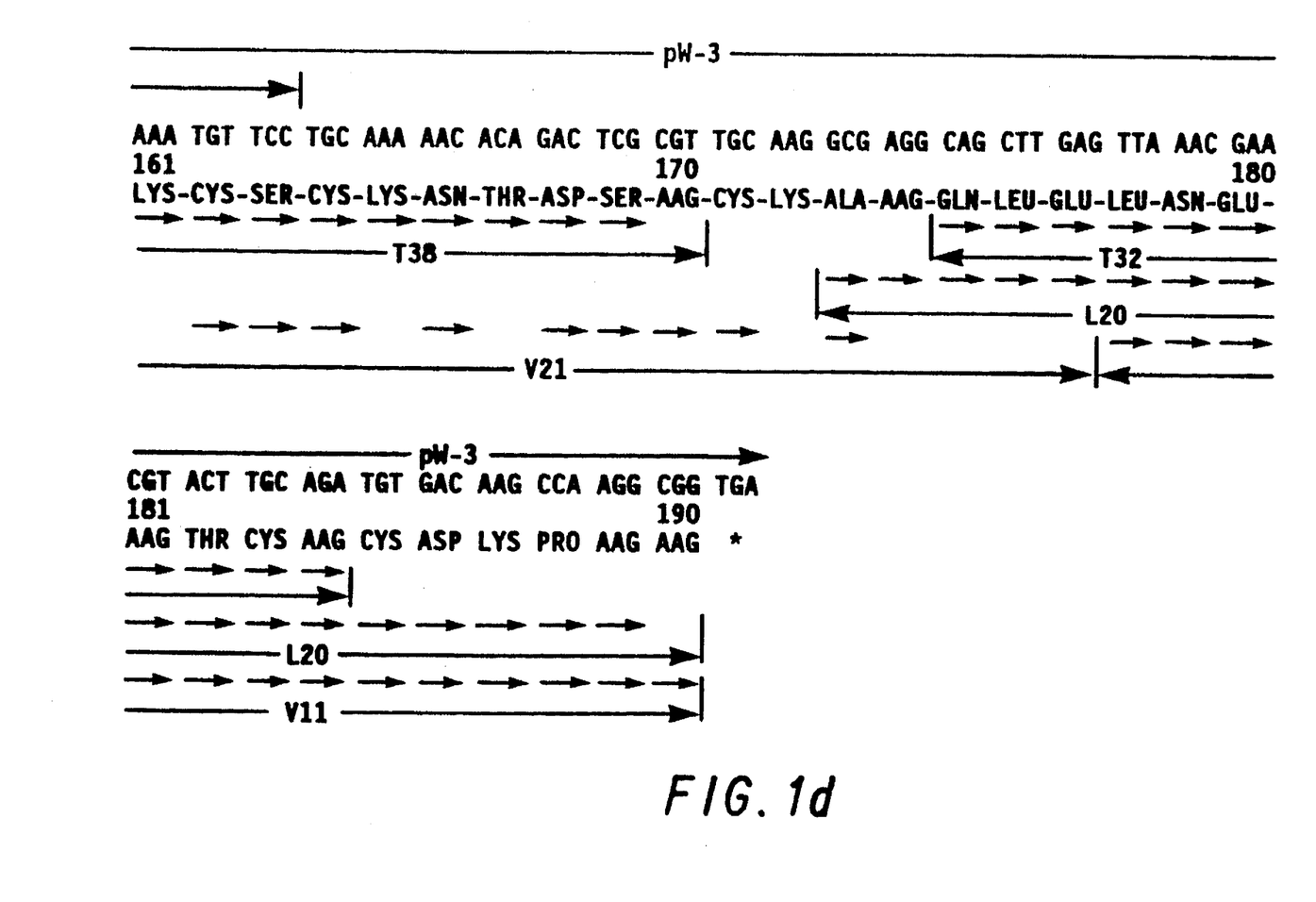

The full length 190 amino acid residue protein translation product and its cDNA coding sequence are shown in FIG. 1. The mature amino terminus begins at residue 27, immediately following a typical hydrophobic secretory leader sequence. A single potential N-gylcosylation site exists at $Asn_{100}$. Most (143 amino acid residues) of the 164 residues of the reduced and carboxymethylated mature subunit including the amino terminus and HPLC reversed phase-purified products of tryptic (T), Lys-C (L), Staphylococcus, aureus V8 protease (V8) and cyanogen bromide (CB) cleavages, were determined by direct microsequencing (Applied Biosystems 470A) using a total of 5 µg of protein. All residues identified by amino acid sequencing are denoted by arrows pointing to the right either directly beneath the lised sequence following the bracket at residue 27 for the amino terminal determination of the whole subunit or, for residues identified from the polypeptide cleavage products, above the double-headed arrows spanning the length of the particular polypeptide. One listed pair of polypeptides, V18A and V18B, was sequenced as a mixture and, therefore, are only confirmatory of the cDNA-deduced amino acid sequence, see figure.

The full length coding region was determined from three sets of overlapping cDNA clones. Degenerate oligonucleotide primers based on the amino acid sequences Phe-Met-Asp-Val-Tyr-Gln from polypeptide L42 (residues 42–47) and Cys-Lys-Asn-Thr-Asp from polypeptide T38 (residues 164–168) were used to PCR amplify the central region of the cDNA for GDGF following the procedure of Saiki et al., Science 230:1350–1354 (1985). A single band migrating at 420 bp was gel purified, digested with SalI, ligated into pGEM3Zf(+) and sequenced. The nucleotide sequence obtained (p4238) was used to design antisense and sense PCR primers to amplify the 5' and 3' ends of the cDNA according to the protocol described by Frohman et al. Proc. Natl. Acad. Sci. USA 85:8998–9002 (1988). These 5' and 3' clones are denoted p5-15 and pW-3, respectively. Regions of complete DNA sequences, excluding the primers, determined for each set of clones are indicated by double-headed arrows above the nucleotide sequence.

It is intended that the nucleotide sequence for glioma-derived growth factor be interpreted to include all codons that code for the appropriate amino acid in the sequence for glioma-derived growth factor, as indicated by the degeneracy of the genetic code. It is further intended that the nucleotide sequence and the amino acid sequence for glioma-derived growth factor include truncated genes or proteins which result in a protein which exhibits biological activity similar to glioma-derived growth factor.

Expression of the GDGF gene is accomplished by a number of different promoter-expression systems and in a number of different cells. Expression vectors are defined herein as DNA sequences that are required for the transcription of cloned copies of recombinant DNA sequences or genes and the translation of their mRNAs in an appropriate host. Such vectors can be used to express genes in a variety of hosts such as bacteria, blue-green algae, yeast cells, insect cells, plant cells and animal cells.

The ability of GDGF to stimulate the division of vascular endothelial cells makes this peptide in all microheterogeneous forms useful as a pharmaceutical agent. The protein as used herein is intended to include all microheterogeneous forms as previously described. The protein can be used to treat wounds of mammals including humans by the administration of the novel protein to patients in need of such treatment.

The novel method for the stimulation of vascular endothelial cells comprises treating a sample of the desired vascular endothelial cells in a nutrient medium with mammalian GDGF, preferable human or rat, at a concentration of about 1–10 ng/ml. If the vascular endothelial cell growth is conducted in vitro, the process requires the presence of a nutrient medium such as DMEM or a modification thereof and a low concentration of calf or bovine serum such as about 0 to 2% by volume. Preservatives such as antibiotics may also be included, these are well known in the art.

The novel growth factor of this invention is useful for the coverage of artificial blood vessels with vascular endothelial cells. Vascular endothelial cells from the patient would be obtained by removal of a small segment of peripheral blood vessel or capillary-containing tissue and the desired cells would be grown in culture in the presence of GDGF and any other supplemental components that might be required for growth. After growth of adequate numbers of endothelial cells in culture to cover a synthetic polymeric blood vessel the cells would be plated on the inside surface of the vessel which is then implanted in the patient. Alternatively, tubular supports are coated in vitro with GDGF prior to implantation into a patient. Following implantation endothelial cells migrate into and grow on the artificial surface. Prior coating of the artificial vessel either covalently or noncovalently, with proteins such as fibrin, collagen, fibronectin or laminin would be performed to enhance attachment of the cells to the artificial surface. The cell-lined artificial vessel would then be surgically implanted into the patient and, being lined with the patients own cells, would be immunologically compatible. The non-thrombogenic endothelial cell lining should decrease the incidence of clot formation on the surface of the artificial vessel and thereby decrease the tendency of vessel blockage or embolism elsewhere.

The novel protein is also useful for the production of artificial vessels. Vascular endothelial cells and smooth muscle cells form the patient would be obtained and grown separately in culture. The endothelial cells would be grown in the presence of GDGF as outlined above. The smooth muscle would be grown in culture by procedures well known in the art. A tubular mesh matrix of a biocompatible polymer (either a synthetic polymer, with or without a coating of proteins, or a non-immunogenic biopolymeric material such as surgical suture thread) would be used to support the culture growth of the smooth muscle cells on the exterior side and vascular endothelial cells on the interior surface. Once the endothelial cells form a confluent monolayer on the inside surface and multiple layers of smooth muscle cells cover the outside, the vessel is implanted into the patient.

The novel peptide can also be used for the induction of tissue repair or growth. The pure GDGF would be used to induce and promote growth of tissue by inducing vascular growth and/or repair. The peptide can be used either topically for tissue repair or intravascularly for vascular repair. For applications involving neovascularization and healing of surface wounds the formulation would be applied directly at a rate of about 10 ng to about 1 ng/cm$^2$/day. For vascular repair GDGF is given intraveneously at a rate of about 1mg to about 100 µg/kg/day of body weight. For internal vascular growth, the formulation would be released directly into the region to be neovascularized either from implanted slow release polymeric material or from slow release pumps. The release rate in either case is about 100 ng to about 100 µg/day/cm$^3$.

For non-topical application the GDGF is administrated in combination with pharmaceutically acceptable carriers or diluents such as, phosphate buffer, saline, phosphate buffered saline, Ringer's solution, and the like, in a pharamaceutical composition, according to standard pharmaceutical practice. For topical application, various pharmaceutical formulations are useful for the administration of the active compound of this invention. Such formulations include, but are not limited to, the following: ointments such as hydrophilic petrolatum or polyethylene glycol ointment; pastes which may contain gums such as xanthan gum; solutions such as alcoholic or aqueous solutions; gels such as aluminum hydroxide or sodium alginate gels; albumins such as human or animal albumins; collagens such as human or animal collagens; celluloses such as alkyl celluloses, hydroxy alkyl celluloses and alkylhydroxyalkyl celluloses, for example methylcellulose, hydroxyethyl cellulose, carboxymethyl cellulose, hydroxypropyl methylcellulose, and hydroxypropyl cellulose; polyoxamers such as Pluronic® Polyols exemplified by Pluronic® F-127; retronits such as tetronic 1508; and alginates such as sodium alginate.

The following examples illustrate the present invention without, however, limiting the same thereto.

EXAMPLE 1

Preparation of Medium Conditioned By GS-9L Cells

GS-9L cells were grown to confluence in 175 cm$^2$ tissue culture flasks in Dulbecco's Modified Eagle's Medium/10% newborn calf serum (DMEM/NCS). At confluence the medium was decanted from the flasks, the flasks were washed with calcium and magnesium free phosphate buffered saline (PBS) and the cells are removed by treatment with a 1X solution of trypsin/EDTA. The cells (1×10$^8$) were pelleted by centrifugation, resuspended in 1500 ml. of DME/5% NCS and plated into a ten level (6000 cm$^2$ surface area) cell factory (NUNC). After 72 hours incubation at 37° C. in a 5% CO$_2$ atmosphere the medium was decanted and the cell factories were washed 3X with PBS. The cells were refed with 1500 ml of a 1:2 mixture of Ham's F-12/DMEM containing 25 mMHepes, 5 micrograms/ml insulin, 10 micrograms/ml transfertin and 1.0 mg/ml bovine serum albumin. This medium was changed with fresh F-12/DMEM after 24 hours and collected every 48 hours after that. The conditioned medium was filtered through a Whatman #1 paper to remove cell debris and stored frozen at −20° C.

EXAMPLE 2

Carboxymethyl-Sephadex Chromatography

GS-9L conditioned medium, from Example 1, was thawed and brought to pH 6.0 with 1M HC1.0he gram of CM Sephadex C-50 cation exchange resin pre-equilibrated in PBS adjusted to pH 6.0 with 1N HCl is added to 20 liters of conditioned medium. The mixture was stirred at low speed for 24 hours at 4° C. The resin was then allowed to settle and the medium is siphoned off. The remaining resin slurry was packed into a 3.0 cm diameter column and any remaining medium is allowed to drain off. Unbound protein was washed off the column with 0.05M sodium phosphate pH 6.0 containing 0.15M NaCl. Glioma-derived growth factor activity was eluted from the column with a subsequent wash of 0.05M sodium phosphate, pH 6.0, containing 0.6M NaCl.

EXAMPLE 3

Concanavalin A Affinity Chromatography

A 1.5 cm diameter column containing 5 ml. packed volume of Con A agarose (Vector Laboratories) is washed and equilibrated with 0.05M NaAcetate pH 6.0 containing 1 mM CaCl$_2$, 1 mM MnCl$_2$ and 0.6M NaCl. The CM Sephadex C-50 eluate containing the GDGF activity, from Example 2, was applied to the column and unbound protein was removed from the column with a wash of equilibration buffer. GDGF activity was eluted from the column by a wash of equilibration buffer containing 0.5M α-methyl mannoside.

EXAMPLE 4

Polyaspartic Acid WCX Cation Exchange Chromatography

A 4.5 mm×250 mm Polyaspartic Acid WCX cation exchange HPLC column (Nest Group) was equilibrated in 0.05M sodium phosphate, pH 6.0. The GDGF activity eluted from the Con A agarose, from Example 3, was applied to the Polyaspartic Acid column at 0.5 ml/min. The column was then eluted with a linear gradient of 0 to 100% B buffer over 30 minutes where A=equilibration buffer and B=A containing 0.75M NaCl. The flow rate was maintained at 0.75 ml/min and fractions are taken every minute. GDGF activity was found in the fractions eluted between 25 and 30 minutes.

EXAMPLE 5

Reverse Phase HPLC Chromatography

The fractions containing GDGF activity eluted from the Polyaspartic Acid column, Example 4, were loaded onto a 4.5×50 mm Vydac C4 reverse phase HPLC column which was previously washed with 0.1% trifluoroacetic acid (TFA)

solution. The column was eluted with a linear gradient over 60 minutes of 0 to 100% B where A=0.1% TFA and B=33% A, 67% acetonitrile. The flow rate was maintained at 0.75 ml/min and fractions are collected every minute. The homogeneous GDGF eluted from the C4 column under So these conditions between 29 and 32 minutes into the gradient. The growth factor was eluted into 150 µl of 1M HEPES buffer, pH 7.55, per 750 µl of column eluate in order to maintain mitogenic activity. SDS-PAGE analysis of the protein on silverstained gels showed GDGF to consist of 3 bands under non-reducing conditions of apparent molecular mass 48,000, 46,000 and 44,000 daltons. Apparent molecular mass was calculated from calibrated protein standards of known molecular mass. All procedures are well known in the art. Under reducing conditions GDGF appears as a single band of protein with a molecular weight of 21,000.

EXAMPLE 6

Mitogenic Assays

Human umbilical vein endothelial cells were plated on gelatin-coated 48 well tissue culture dishes at a density of 2000 cells/well in 500 µl of Medium 199 containing 20% heat inactivated fetal calf serum (FCS) and 15 mM Hepes buffer. Samples of GDGF, from Examples 1–5, to be assayed were serially diluted in M199/fetal calf serum and added to the wells at the time of plating. The culture plates are incubated at 37° C. in 5% $CO_2$ for 72 hours. After incubation the medium was removed from the cells, which are then rinsed with 250 µl of PBS and the cells are detached with 200 µl of trypsin (0.1%)/EDTA (0.04%). The cells were then counted in a hemocytometer.

Bovine aortic endothelial cells were plated in 48 well plates at a density of 2000 cells/well in 500 microliters of DMEM/10% NCS and incubated at 37° C. for 12 hours. The medium was removed from the plates and replaced with DMEM/1% heat inactivated FCS and the cells are again incubated for 48 hours. Samples of GDGF, from Examples 1–5, to be assayed were serially diluted in DMEM/1%FCS and added to the plates at the end of this 48 hour period. After a further 12 hours of incubation 1.6 µCi of [methyl-$^3$H]thymidine (20 Ci/mmol) and 2.45 µg of unlabeled thymidine per milliliter of medium was added to the wells in 20 µl of DMEM. The plates were incubated again for 36 hours, the medium is removed, the cell layers were washed with PBS and the cells were lysed with 250 µl of a solution of 2 grams sodium carbonate and 0.4 grams NaOH per 100 ml. The amount of incorporation of radiolabel into DNA was then determined by scintillation counting.

The concentration of GDGF which elicited a half-maximal mitogenic response in HUVE cells was approximately 1 ng/ml. The glycosaminoglycan heparin, which is required in these assays at a level of 10–100 µg/ml to promote a response to a positive control, acidic fibroblast growth factor, does not enhance mitogenic stimulation of these cells by GDGF.

Utilizing the mitogenic assay for BALB/C 3T3 fibroblasts as described by Linemeyer et al., Bio/Tech. 5:960–965 (1987), GDGF was unable to stimulate a mitogenic response in 3T3 cells. Employing the biochemical procedures and analytical techniques described above, the stepwise purification is summarized in Table 1.

TABLE I

Purification of Glioma-Derived Growth Factor

| Purification Step | Protein (mg) | Units (mg/ml) | Sp. Activity (units/mg) | Purification Factor |
|---|---|---|---|---|
| Conditioned Medium CM Sephadex | $2.5 \times 10^3$ | 20,000 | 8 | 1 |
| C-50 | 16 | 12,000 | $7.5 \times 10^2$ | 94 |
| Con A | 1.2 | 4,000 | $3.3 \times 10^3$ | 417 |
| Polyaspartic Acid WCX | $1.1 \times 10^{-2}$ | 1,500 | $1.4 \times 10^5$ | 17,500 |
| $C_4$ HPLC | $1.0 \times 10^{-3}$ | 1,000 | $1.0 \times 10^6$ | 125,000 |

[1]Based on 5 L of conditioned medium

EXAMPLE 7

Amino Acid Composition And Sequence

Both samples of the native dimeric GDGF and a sample of the reduced and carboxymethylated monomer have been hydrolyzed and their amino acid compositions determined using the Waters PicoTag system. Both samples of the native dimeric GDGF and a sample of reduced and carboxymethylated monomer (generated by reduction and carboxymethylation of GDGF using the protocol listed below for the amino acid sequence determination) were hydrolyzed in constant boiling HCl containing 1% phenol (Pierce) for 24 hr at 110° C. The hydrolysate was subsequently derivatized with phenylisothiocyanate to yield the phenylthiocarbamyl amino acids (PTC). The PTC amino acids were resolved by reverse phase chromatography on a Waters PicoTag amino acid analysis HPLC column and quantitated by comparison of their absorbances at 254 nm to standard PTC amino acids of known amount. The exact protocol is detailed in Waters PicoTag Amino Acid Analysis System manual No. 88140, February, 1986. The amino acid composition is based on a molecular mass of 35,000 daltons for the dimeric form of GDGF minus oligosaccharide chains. The amount of oligosaccharide present on GDGF was determined by comparing the molecular mass of GDGF in reducing SDS-PAGE before and after removal of oligosaccharides with the enzyme Endoglycosidase H. Twenty-five ng of pure GDGF in 0.05M sodium citrate, pH 6.0, 0.01% SDS and 0.1M beta-mercaptoethanol, was treated with 20 mU/ml of Endoglycosidase H for 6 hr at 37° C. The product was subsequently electrophoresed in 12.5% SDS-PAGE and silver stained to determine the alteration in relative mobility due to oligosaccharide removal in order to establish the effect of the oligosaccharide sidechains on protein molecular mass estimates. The results are shown in the following table.

TABLE 2

Amino Acid Composition Of Dimeric GDGF

| Amino Acid | Units |
|---|---|
| Asp | 20 |
| Glu | 44 |
| Ser | 24 |
| Gly | 10 |
| His | 10 |
| Arg | 24 |
| Thr | 18 |
| Ala | 12 |
| Pro | 28 |
| Tyr | 8 |
| Val | 16 |

TABLE 2-continued

Amino Acid Composition Of Dimeric GDGF

| Amino Acid | Units |
| --- | --- |
| Phe | 8 |
| Met | 8 |
| Cys | 28 |
| Ile | 12 |
| Leu | 14 |
| Lys | 18 |

Tryptophan has not been determined. Cystine was estimated from the level of incorporation of $^{14}$C-iodoacetic acid into the reduced and carboxymethylated monomer.

A 4 μg sample of native dimeric GDGF was reduced in 0.1M Tris, pH 9.5, with 0.1% EDTA, 6M guanidinium chloride and 20 mM dithiothreitol for 2 hr at 50° C. The reduced protein was carboxymethylated by the addition of 9.2 μM of unlabeled and 2.8 μM of $^{14}$C-iodoacetic acid in 0.7 M Tris pH 7.8 containing 0.1% EDTA and 6M guanidinium chloride. The protein was carboxymethylated for 1 hr at room temperature. The protein was subsequently reisolated by $C_4$ RP-HPLC as described above. A sample of the reduced and carboxymethylated monomer was treated with either the protease trypsin or Lys C. For trypsin, reduced and carboxymethylated GDGF was treated with a 1:100 ratio by weight of tosylphenylchloroketone-trypsin to GDGF in 0.1M ammonium bicarbonate, pH 8.3 for 6 hr at 37° C. The resultant peptide fragments were resolved by chromatography on a 4.5 mm×25 cm $C_{18}$ reverse phase column. Peptides were eluted with a linear gradient over 3 hr of 0–100% B where A=0.1 TFA and B=0.1% TFA containing 67% acetonitrile. For Lys C cleavage all conditions were identical except that the buffer used was 0.1M Tris, pH 8.5, a 40:1 ratio of GDGF to Lys C was maintained and the GDGF and Lys C mixture was incubated for 14 hr. The amino acid sequences of the isolated peptides were then determined using Edman degradation in an ABI gas phase sequenator in conjunction with the ABI 120 A on line phenylthiohydantoin analyzer (Applied Biosystems Int.). The peptide sequences are shown in the following table.

TABLE 3

Amino Acid Sequences

Trypsin

T22
Thr—Lys—Pro—Glu—Asn—His—Cys—Glu—Pro—
Cys—Ser—Glu—Arg—Arg—Lys
T27
Xxx[a]—Xxx—Thr—Thr—Glu—Gly—Glu—Gln—Lys—Ala—
His—Glu—Val—Val—Lys
T38
His—Leu—Phe—Val—Gln—Asp—Pro—Gln—Thr—
Cys—Lys—Cys—Ser—Cys—Lys—Asn—Thr—Asp
T40
Phe—Met—Asp—Val—Tyr—Gln—Arg

Lys C

L16
Asp—Arg—Thr—Lys—Pro—Glu—Asn—His—Cys—
Glu—Pro—Cys—Ser—Glu—Arg—Arg—Lys
L20
Ala—Arg—Gln—Leu—Glu—Leu—Asn—Glu—Arg—
Thr—Cys—Arg—Cys—Asp—Lys—Pro—Arg
L23
His—Leu—Phe—Val—Gln—Asp—Pro—Gln—Thr—
Cys—Lys

[a]denotes an unidentified amino acid residue.

The amino acid sequences of the isolated peptides illustrates the unique nature of GDGF.

GDGF was stored a 4° C. in the aqueous trifluoroacetic acid (TFA)/acetonitrile mixture used to elute the homogeneous protein in reversed phase $C_4$ HPLC chromatography at the final stage of the purification protocol previously described. Aliquots of the purified protein (1–2 μg) were vacuum evaporated to dryness is acid-washed 10×75 mm glass tubes and reduced for 2 hours at 50° C. in 100 μl of 0.1M Tris buffer, pH 9.5, and 6M guanidinium chloride containing 0.1% EDTA and 20 mM dithiothreitol (Calbiochem, Ultrol grade) under an argon atmosphere. The reduce protein was subsequently carboxymethylated for 1 hour at 20° C. by the addition of 100 μl of 0.7M Tris, pH acid and 50 μCi of iodo[2-$^{14}$C]acetic acid (17.9 mCi/mmole, Amersham). After completion of the carboxymethylation, the mixture was loaded directly onto a 4.6 mm×5.0 cm Vydac $C_4$ column which had been preequilibrated in 0.1% TFA. The reduced and carboxymethylated protein was repurified by elution with a 30 minute linear gradient of 0 to 67% (v/v) acetonitrile in 0.1% TFA at a flow rate of 0.75 ml/min and stored in this elution solution at 4° C.

Reduced and carboxymethylated GDGF (725 ng) was dried by vacuum evaporation in an acid-washed 10 ×75 mm glass tube. TPCK-treated bovine pancreatic trypsin (30 ng, Worthington) was added in 200 μl of 0.1M ammonium bicarbonate, pH 8.3. The substrate protein was digested at 37° C. for 6 hours and the resulting polypeptides loaded onto a 4.6 mm×25 cm Vydac $C_{18}$ reversed phase HPLC column equilibrated in 0.1% TFA. Polypeptides generated by proteolysis on the carboxyl terminal side of arginine and lysine residues were fractionated by elution with a 2 hour linear gradient of 0–67% acetonitrile in 0.1% TFA at a flow rate of 0.75 ml/min at 20° C. Individual peaks were of 0.75 ml/min and stored in this elution solution at 4° C.

Reduced and carboxymethylated GDGF (925 ng) was dried by vacuum evaporation in an acid-washed 10 ×75 mm glass tube. Lys C protease (50 ng, Boehringer Mannhelm), an enzyme that cleaves on the carboxyl terminal side of lysine residues, was added in 50 μl of 0.1M Tris, pH 8.5, 1 mM EDTA. The substrate protein was digested at 37° C. for 8 hours and the resulting polypeptides resolved by reversed phase HPLC chromatography on a $C_{18}$ column as described above.

Reduced and carboxymethylated GDGF (1.1 μg) was dried and solubilized in 5 μl of 0.7M Tris, pH 7.8, 6M guanidinium chloride containing 0.1% EDTA. V8 protease (65 ng, Miles Labs) was added in 65 μl of 0.1M ammonium bicarbonate, pH 8.0, 0.1% EDTA and the mixture was incubated for 48 hours at 37° C. Under these digestion conditions, this protease cleaves predominantly on the carboxyl terminal side of glutamic acid residues. The resulting polypeptides were resolved by reversed phase HPLC chromatography on a $C_{18}$ column as described above.

Following reduction and carboxymethylation of GDGF (1.3 μg) the protein solution was adjusted to pH 6.8 with 6 N HCl and dithiothreitol was added to a final concentration of 2M for reduction of any methionine sulfoxide to methionine residues. Following 20 hours of reduction at 39° C. the protein was repurified on a $C_4$HPLC reversed phase column as previously described. The product was dried in a 10 ×75 mm glass tube and cleaved on the carboxyl terminal side of methionine residues by 200 μl of 40 mM cyanogen bromide in 70% (v/v) formic acid under an argon atmosphere at 20° C. for 24 hours in the dark. The cleavage products were resolved by reversed phase HPLC chromatography on a $C_{18}$ column as previously described.

EXAMPLE 8

PCR Amplification, Cloning and Sequencing of P4238

Two degenerate oligonucleotides were synthesized in order to amplify the cDNA encoding the peptide sequences of GDGF between lysC fragment 42 and tryptic fragment 38. These oligonucleotides were:

42.2 5' TTTGTCGACTT[TC]ATGGA[TC]GT[N]TA[TC]CA3'

T383'B 5' CAGAGAATTCGTCGACA[AG]TC[N]GT[AG]TT[TC]TT[AG]CA3' where N=ACGT

RNA was isolated from GS9L cells using the Fast Track RNA isolation kit from Invitrogen and the protocol provided. First strand cDNA synthesis was performed as follows;

1 microgram of GS9L RNA was annealled to 1 pg of adapter primer TA17, 5' GACTCGAGTCGACATC-GATTTTTTTTTTTTTTTTTT 3', by incubating in a volume of 10 μl at 70C for 5 min. followed by cooling to room temperature. To this reaction was added

| |
|---|
| 3.0 μl water |
| 2.5 μl 10X buffer (500 mM Tris-HCl pH 8.3, 750 mM KCl, 100 mM Mg Cl12, 5 mM spermidine) |
| 2.5 μl 100 mM DTT |
| 2.5 μl 10 mM each dATP, dGTP, dCTP, dTTP |
| 0.6 μl 15 units RNasin |
| 2.5 μl 40 mM Na pyrophosphate |
| 1.5 μl 15 units reverse transcriptase |

The reaction was incubated at 42° C. for 1 hour, then diluted to 1 ml in 10mM Tris-HCl 1 mM EDTA pH 7.5

| PCR Reactions |
|---|
| Primary reaction 100 μl |
| 10 μl 10X buffer from Perkin Elmer Cetus GeneAmp kit |
| 16 μl 1.25 mM each stock of dATP, dCTP, dGTP, and dTTP |
| 2 μl first strand GS9L cDNA |
| 2 μl 50 pMoles L42.2 |
| 2 μl 50 pMoles T383'B |
| 0.5 μl 2.5 units Amplitaq DNA polymerase |
| 67.5 μl water |

Reaction conditions 40 cycles of 94C 1'; 50C 2'30"; 72C 2'

| Prep scale secondary reaction |
|---|
| 100 μl 10X buffer |
| 160 μl 1.25 mM each stock of dATP, dCTP, dGTP, and dTTp |
| 10 μl primary PCR reaction |
| 20 μl 500 pMoles L42.2 |
| 20 μl 500 pMoles T383'B |
| 5 μl 25 units Amplitaq DNA polymerase |
| 685 μl water |

Reaction conditions 94C 1'; 55C 2'; 72C 2' 30 cycles

The PCR product was concentrated by Centricoh 30 spin columns, purified on a 1% agarose gel, and digested with restriction endonuclease SalI. The SalI fragment was then ligated into SalI cut pGEM3Zf(+). The ligation mix was used to transform *E. coli* XL-1 blue. Plasmid DNA was isolated from white transformants and sequenced by the dideoxy chain termination method.

EXAMPLE 9

PCR Amplification, Cloning and Sequencing of pW-3

Based on the sequence obtained from the p4238 clones, two specific PCR primers were synthesized; oligo307 5'TTTGTCGACTCAGAGCGGAGAAAGC 3' and oligo289 5' TTTGTCGACGAAAATCACTGTGAGC 3'. These primers were used in combination with oligoA17 5' GACTCGAGTCGACATCG 3' to amplify the cDNA encoding the C00H terminus of GDGF using the 3' RACE technique described by Frohman et al., PNAS 85: 8998–9002 (1988).

| PCR reactions |
|---|
| Primary reaction 100 μl |
| 10 μl 10X buffer from Perkin Elmer Cetus GeneAmp kit |
| 18 μl 1.25 mM each stock of dATP, dCTP, dGTP, and dTTP |
| 0.35 μl first strand GS9L cDNA |
| 2 μl 50 pMoles 289 |
| 0.5 μl 2.5 units Amplitaq DNA polymerase |
| 67.15 μl water |

Reaction conditions 94C 1'; 58C 2'; 72C 2' 10 cycles then add 50pMoles A17, then 1 cycle of 94C 1'; 58C 2'; 72C 40' followed by 40 cycles 94C 1'; 58C 2'; 72C 2'.

| Prep Scale secondary reaction |
|---|
| 60 μl 10X buffer |
| 108 μl 1.25 mM each stock of dATP, dCTP, dGTP, and dTTP |
| 24 μl primary PCR reaction |
| 12 μl 300 pMoles 307 |
| 12 μl 300 pMoles A17 |
| 3 μl 15 units Amplitaq DNA polymerase |
| 381 μl water |

Reaction conditions 94C 1'; 58C 2'; 72C 2' 30 cycles

The PCR product was purified on a 1% agarose gel and digested with restriction endonuclease SalI. The SalI fragment was then ligated into SalI cut pGEM3Zf(+). The ligation mix was used to transform *E. coli* XL-1 blue. Plasmid DNA was isolated from white transformants and sequenced by the dideoxy chain termination method.

EXAMPLE 10

PCR Amplification, Cloning and Sequencing of p5-15

Bsed on the sequence of p4238 clones, two specific PCR primers were synthesized; oligo113 5'TTTGTCGACAA-CACAGGACGGCTTGAAG 3' and oligo74 5' TTTGTC-GACATACTCCTGGAAGATGTCC 3'. These primers were used in combination with oigoA17 5' GACTCGAGTCGA-CATCG 8' to amplify the cDNA encoding the amino terminus of GDGF using the 5' RACT technique described by Frohman et al., supra. Oligo 151 was synthesized in order to specifically prime GDGF cDNA from GS9L RNA. Oligo 151 is 5' CTTCATCATTGCAGCAGC 3'.

RNA was isolated from GS9L cells using the Fast Track RNA isolation kit from invitrogen using the protocol provided. First strand cDNA synthesis was performed as follows;

1 microgram of GS9L RNA was annealled to 1 microgram of oligo151 by incubating in a volume of 6 microliter at 70C for 5' followed by cooling to room temperature. To this reaction was added

| |
|---|
| 1.5µl 10X buffer (500 mM Tris-HCl pH 8.3, 750 mM KCl, 100 mM MgCl2, 5 mM spermidine) |
| 2.5 µl 10 mM DTT |
| 2.5 µl 10 mM each dATP, dGTP, dCTP, dTTP |
| 0.6 µl 25 units RNasin |
| 2.5 µl 40 mM Na pyrophosphate |
| 9.5 µl 20 units diluted reverse transcriptase |

The reaction was incubated at 42C for 1 hour. Excess oligo151 was removed by Centricon 100 spin columns and the 5' end of the cDNA was tailed by the addition of dATP and terminal transferase. The tailed cDNA was diluted to a final volume of 150 µl in 10mM Tris-HCl, 1 mM EDTA pH 7.5

| PCR Reactions |
|---|
| Primary reaction 50 µl |
| 5 µl 10X buffer from Perkin Elmer Cetus GeneAmp Kit |
| 8 µl 1.25 mM each stock of dATP, dCTP, dGTP, and dTTP |
| 5 µl first strant GS9L cDNA prime with oligo151 and tailed |
| 1 µl 25 pMoles olgo113 |
| 1 µl 25 pMoles A17 |
| 1 µl 10 pMoles TA17 |
| 0.25 µl 1.225 units Amplitq DNA |

| PCR Reactions |
|---|
| polymersase 28.75 ξl water |

Reaction conditions; 1 cycle 94C 1'; 50C 2'; 72C 40' then 40 cycles of 94C 1'; 50C 1 '30"; 72C 2'

| Prep scale secondary reaction |
|---|
| 60 µl 10X buffer |
| 96 µl 1.25 mM each stock of dATP, dCTP, dGTP, and dTTP |
| 6 µl primary PCR reaction |
| 12 µl 300 pMoles oligo74 |
| 12 µl 300 pMoles A17 |
| 3 µl 15 units Amplitaq DNA polymerase |
| 411 µl water |

Reaction conditions 94C 1'; 55C 2'; 72C 2' 30 cycles

The PCR product was concentrated by Centricon 100 spin columns, and digested with restriction endonuclease SalI. The SalI fragment was then ligated into SalI cut pGEM3Zf(+). The ligation mix was used to transform *E. coli* XL-1 blue. Plasmid DNA was isolated from white transformants and sequenced by the dideoxy chain termination method. The base sequence is shown in FIG. 1.

What is claimed is:

1. An isolated and purified rat glioma derived growth factor which is mitogenic for mammalian endothelial cells, having a molecular mass range of approximately 44,000 to 48,000 daltons, wherein said growth factor has the amino acid composition set forth in Table 2.

2. An isolated and purified glioma derived growth factor which is mitogenic for mammalian endothelial cells, wherein said growth factor is characterized by the amino acid sequence set forth in the Figure.

* * * * *